United States Patent
Pitner et al.

(10) Patent No.: US 7,326,538 B2
(45) Date of Patent: *Feb. 5, 2008

(54) BINDING PROTEINS AS BIOSENSORS

(75) Inventors: J. Bruce Pitner, Durham, NC (US); Jason E. Gestwicki, Mountain View, CA (US); Zachary A. Pfieffer, Madison, WI (US); Helen V. Hsieh, Durham, NC (US)

(73) Assignee: Becton Dickinson and Company, Franklin Lakes, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/424,894

(22) Filed: Jun. 19, 2006

(65) Prior Publication Data

US 2006/0216753 A1   Sep. 28, 2006

Related U.S. Application Data

(63) Continuation of application No. 10/039,799, filed on Jan. 4, 2002, now Pat. No. 7,064,103.

(51) Int. Cl.
*G01N 33/53* (2006.01)
(52) U.S. Cl. .................................... 435/7.1; 435/287.2
(58) Field of Classification Search ...................... None
See application file for complete search history.

(56) References Cited

U.S. PATENT DOCUMENTS

| | | | |
|---|---|---|---|
| 4,704,029 A | 11/1987 | Van Heuvelen | |
| 6,197,534 B1 * | 3/2001 | Lakowicz et al. | 435/14 |
| 6,277,627 B1 * | 8/2001 | Hellinga | 435/287.1 |
| 6,432,723 B1 | 8/2002 | Plaxco et al. | |
| 6,576,430 B1 | 6/2003 | Hsieh et al. | |
| 7,064,103 B2 * | 6/2006 | Pitner et al. | 514/2 |
| 2002/0004217 A1 | 1/2002 | Hellinga | |
| 2006/0216752 A1 * | 9/2006 | Pitner et al. | 435/7.1 |

FOREIGN PATENT DOCUMENTS

WO    99/34212    7/1999

OTHER PUBLICATIONS

Sota et al., Detection of Conformational Changes in an Immobilized Protein Using Surface Plasmon Resonance, Anal. Chem., 70, May 10, 1998, pp. 2019-2024.
Gestwicki et al., Using Receptor Conformational Change to Detect Low Molecular Weight Analytes by Surface Plasmon Resonance, Anal. Chem., 73, Dec. 23, 2001, pp. 5732-5737.
Catimel et al., Kinetic Anal. of the Interaction Between the Monoclonal Antibody A33 and its Colonic Epithelial Antigen by the use of an Optical Biosensor, J. Chroma., 776, Jul. 1, 1997, pp. 15-30.
Tolosa et al., Glucose Sensor for Low-cost Lifetime-Based Sensing Using a Genetically Engineered Protein, Anal. Biochem., 267, Feb. 1, 1999, pp. 114-120.
Sigal et al., Self-Assembled Monolayer for the Binding and Study of Histidine-Tagged Proteins by Surface Plasmon Resonance, Anal. Chem., 68, 3, 1996, pp. 490-497.
Turkova, Oriented Immobilization of Biologically Active Proteins as a tool for Revealing Protein Interactions and Function, J. Chroma. 722, Feb. 1-2, 1999, pp. 11-31.
Jones, Mark E. et al., "Bioremediation Monitoring Using Optical Fiber Long Period Grating (LPG)-Based Sensors", NSF Manufacturing Conference, Vancouver, Jan. 2000.
Mowbray, Sherry L., et al., "Structure of the Preplasmic Glucose/Galactose Receptor of Salmonella typhimurium", Receptor, 1990, I, 41-54.
Vyas, Nand K., et al., "Sugar and Signal-Transducer Binding Sites of the *Escherichia coli* Galactose Chemoreceptor Protein", Science, pp. 1290-1295, vol. 242.
Bhatia; Vikram, et al., "Optical Fiber Long-Period Grating Sensors", Optics Letters, pp. 692-694, vol. 21, No. 9 May 1, 1996.
Baird, Cheryl L., et al., "Current and Emerging Commercial Optical Biosensors", Journal of Molecular Recognition, pp. 261-268, 2001; 14, DOI: 10.1002/jmr.544.
Turcatti, Gerardo, et al., "Probing the Structure and Function of the Tachykinin Neurokinin-2 Receptor through Biosynthetic Incorporation of Fluorescent Amino Acids at Specific Sites", The Journal of Biological Chemistry, pp. 19991-19998, vol. 271, No. 33, Issue of Aug. 16, 1996.
Pisarchick, Mary Lee, et al., "Binding of a Monoclonal Antibody and Its Fab Fragment To Supported Phospholipid Monolayers Measured By Total Internal Reflection Fluorescence Microscopy", pp. 1235-1249, Biophysical Journal, vol. 58, Nov. 1990.
Gilardi, Gianfranco, et al., "Engineering the Maltose Binding Protein for Reagentless Fluorescence Sensing", pp. 3840-3847, Analytical Chemistry, vol. 66, No. 21, Nov. 1, 1994.
Topoglidis, Emmanuel, et al., "Protein Adsorption on Nanocrystalline TiO2 Films: An Immobilization Strategy for Bioanalytical Devices", pp. 5111-5113, Analytical Chemistry, vol. 70, No. 23, Dec. 1, 1998.
O'Sullivan, C.K., Commercial Quartz Crystal Microbalances - Theory and Applications, pp. 663-670, 'Biosensors & Bioelectronics, 14(1999).

* cited by examiner

*Primary Examiner*—Cecilia J. Tsang
*Assistant Examiner*—Roy Teller
(74) *Attorney, Agent, or Firm*—Sughrue Mion PLLC

(57) ABSTRACT

The invention is directed to compositions of mutated binding proteins containing thiol groups for coupling to sensor surfaces, analyte biosensor devices derived there from, and methods of their use as analyte biosensors both in vitro and in vivo.

13 Claims, 8 Drawing Sheets

BINDING PROTEINS AS BIOSENSORS

CROSS-REFERENCE TO RELATED APPLICATIONS

This application is a continuation of U.S. Ser. No. 10/039,799, filed Jan. 4, 2002, which issues on Jun. 20, 2006 as U.S. Pat. No. 7,064,103.

BACKGROUND OF THE INVENTION

1. Field of the Invention

The invention is in the field of biotechnology. Specifically, the invention is directed to mutated binding proteins containing thiol groups for coupling to sensor surfaces, analyte biosensor devices derived there from, and their use as analyte biosensors both in vitro and in vivo.

2. Background of the Invention

Monitoring glucose concentrations to facilitate adequate metabolic control in diabetics is a desirable goal and would enhance the lives of many individuals. Currently, most diabetics use the "finger stick" method to monitor their blood glucose levels and patient compliance is problematic due to pain caused by frequent (several times per day) sticks. As a consequence, there have been efforts to develop non-invasive or minimally invasive in vivo and more efficient in vitro methods for frequent and/or continuous monitoring of blood glucose or other glucose-containing biological fluids. Some of the most promising of these methods involve the use of a biosensor. Biosensors are devices capable of providing specific quantitative or semi-quantitative analytical information using a biological recognition element which is combined with a transducing (detecting) element.

The biological recognition element of a biosensor determines the selectivity, so that only the compound which has to be measured leads to a signal. The selection may be based on biochemical recognition of the ligand where the chemical structure of the ligand (e.g. glucose) is unchanged, or biocatalysis in which the element catalyzes a biochemical reaction of the analyte.

The transducer translates the recognition of the biological recognition element into a semi-quantitative or quantitative signal. Possible transducer technologies are optical, electrochemical, acoustical/mechanical or colorimetric. The optical properties that have been exploited include absorbance, fluorescence/phosphorescence, bio/chemiluminescence, reflectance, light scattering and refractive index. Conventional reporter groups such as fluorescent compounds may be used, or alternatively, there is the opportunity for direct optical detection, without the need for a label.

Biosensors specifically designed for glucose detection that use biological elements for signal transduction typically use electrochemical or calorimetric detection of glucose oxidase activity. This method is associated with difficulties including the influence of oxygen levels, inhibitors in the blood and problems with electrodes. In addition, detection results in consumption of the analyte that can cause difficulties when measuring low glucose concentrations.

A rapidly advancing area of biosensor development is the use of fluorescently labeled periplasmic binding proteins (PBP's). As reported by Cass (Anal. Chem. 1994, 66, 3840-3847), a labeled maltose binding protein (MBP) was effectively demonstrated as a useable maltose sensor. In this work MBP, which has no native cysteine residues, was mutated to provide a protein with a single cysteine residue at a position at 337 (S337C). This mutation position was within the binding cleft where maltose binding occurred and therefore experienced a large environmental change upon maltose binding. Numerous fluorophores were studied, some either blocked ligand binding or interfered with the conformational change of the protein. Of those studied IANBD resulted in a substantial increase in fluorescence (160%) intensity upon maltose binding. This result may be consistent with the location of the fluorophore changing from a hydrophilic or solvent exposed environment to a more hydrophobic environment as would have been theoretically predicted for the closing of the hinge upon maltose binding. However this mutant protein and the associated reporter group do not bind diagnostically important sugars in mammalian bodily fluids. Cass also disclosed (Analytical Chemistry 1998, 70(23), 5111-5113) association of this protein onto $TiO_2$ surfaces; however, the surface-bound protein suffered from reduced activity with time and required constant hydration.

Hellinga, et al. (U.S. Pat. No. 6,277,627), reports the engineering of a glucose biosensor by introducing a fluorescent reporter into a Galactose/Glucose Binding Protein (GGBP) mutated to contain a cysteine residue, taking advantage of the large conformation changes that occur upon glucose binding. Hellinga et al (U.S. Pat. No. 6,277,627) disclose that the transmission of conformational changes in mutated GGBPs can be exploited to construct integrated signal transduction functions that convert a glucose binding event into a change in fluorescence via an allosteric coupling mechanism. The fluorescent transduction functions are reported to interfere minimally with the intrinsic binding properties of the sugar binding pocket in GGBP.

In order to accurately determine glucose concentration in biological solutions such as blood, interstitial fluids, ocular solutions or perspiration, etc., it may be desirable to adjust the binding constant of the sensing molecule of a biosensor so as to match the physiological and/or pathological operating range of the biological solution of interest. Without the appropriate binding constant, a signal may be out of range for a particular physiological and/or pathological concentration. Additionally, biosensors may be configured using more than one protein, each with a different binding constant, to provide accurate measurements over a wide range of glucose concentrations as disclosed by Lackowicz (U.S. Pat. No. 6,197,534).

Despite the usefulness of mutated GGBPs, few of these proteins have been designed and examined, either with or without reporter groups. Specific mutations of sites and/or attachment of certain reporter groups may act to modify a binding constant in an unpredictable way. Additionally, a biosensor containing reporter groups may have a desirable binding constant, but not result in an easily detectable signal upon analyte binding. It is clear from the prior art that the overriding factors that determine sensitivity of a particular reporter probe attached to a particular protein for the detection of a specific analyte is the nature of the specific interactions between the selected probe and amino acid residues of the protein. It is not currently possible to predict these interactions within proteins using existing computational methods, nor is it possible to employ rational design methodology to optimize the choice of reporter probes. It is currently not possible to predict the effect on the binding constant based on the position of the reporter group in the protein (or visa-versa).

To develop reagentless, self-contained, and or implantable and or reusable biosensors proteins the transduction element must be in communication with a detection device to interrogate the signal to and from the transduction element. Typical methods include placing the proteins within or onto the surface of optical fibers or planner waveguides using immobilization strategies. Such immobilization strategies include, but are not limited to, entrapment of the protein within semi-permeable membranes, organic polymer matrixes, or inorganic polymer matrixes. The immobilization strategy ultimately may determine the performance of the working biosensor. Prior art details numerous problems associated with the immobilization of biological molecules. For example, many proteins undergo irreversible conformational changes, denaturation, and loss of biochemical activity. Immobilized proteins can exist in a large number of possible orientations on any particular surface, for example, with some proteins oriented such that their active sites are exposed whereas others may be oriented such that there active sites are not exposed, and thus not able to undergo selective binding reactions with the analyte. Immobilized proteins are also subject to time-dependent denaturation, denaturation during immobilization, and leaching of the entrapped protein subsequent to immobilization. Therefore problems result including an inability to maintain calibration of the sensing device and signal drift. In general, binding proteins require orientational control to enable their use, thus physical absorption and random or bulk covalent surface attachment or immobilization strategies as taught in the literature generally are not successful.

Therefore, there is a need in the art to design additional useful mutated proteins and mutated GGBP proteins generating detectable and reversible signals upon analyte binding for use as biosensors, and additionally there is a need in the art to design additional useful mutated binding protein and mutated GGBP's containing thiol groups for attachment to surfaces for generating detectable signals upon analyte or glucose binding for use as biosensors.

SUMMARY OF THE INVENTION

The invention provides a biosensor including a) at least one mutated binding protein and at least one thiol group attached thereto; and b) at least one sensor surface wherein said mutated binding protein is coupled through said thiol group to said surface; wherein said at least one sensor surface provides a detectable signal resulting from a change in refractive index when said mutated binding protein binds to analyte.

Furthermore, the invention provides a method for analyte detection including a) providing at least one mutated binding protein and at least one thiol group attached thereto; b) at least one sensor surface wherein said mutated binding protein is coupled through said thiol group to said surface; c) exposing said mutated binding protein to biological solutions containing varying analyte concentrations; d) detecting a detectable and reversible signal resulting from a change in refractive index; wherein said detectable and reversible signal results from a change in refractive index upon binding corresponding to said varying analyte concentrations.

DETAILED DESCRIPTION OF THE INVENTION

Figure 1:
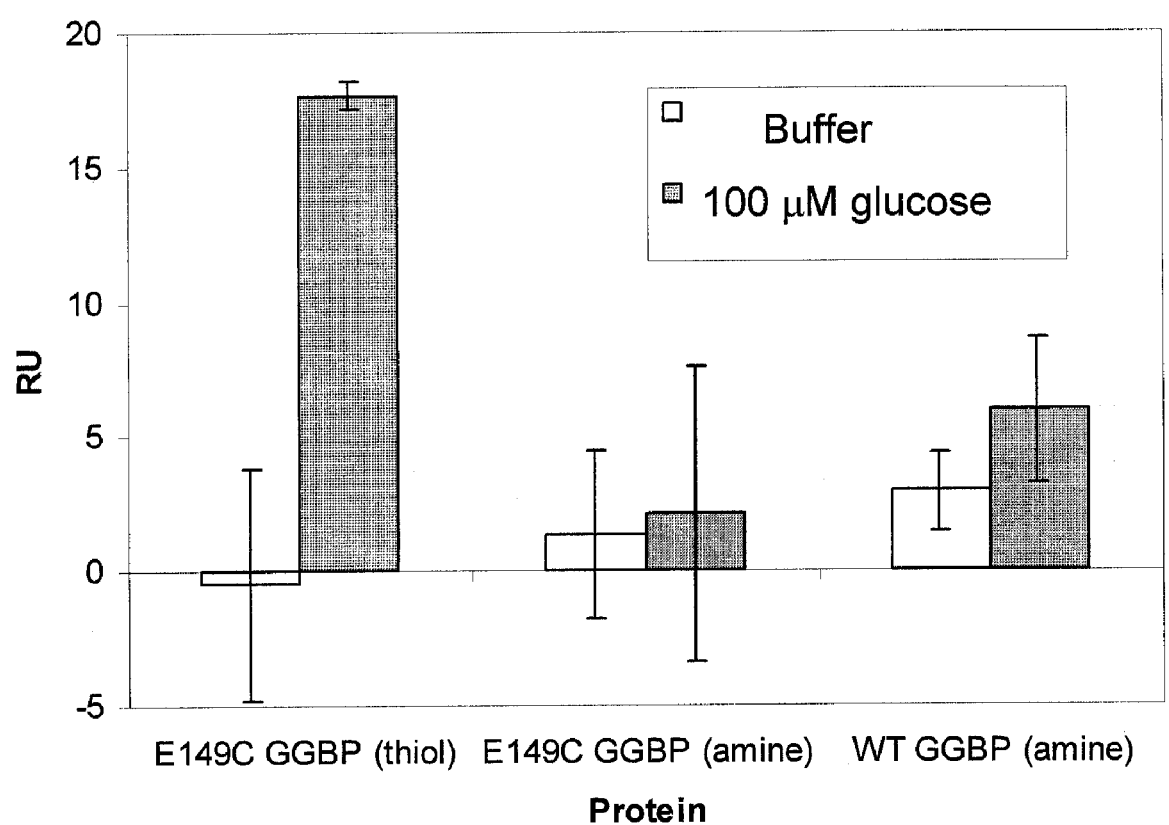
FIG. 1 illustrates glucose detection using SPR utilizing thiol coupled E149C GGBP, amine coupled E149C GGBP, and amine coupled wild type (WT) GGBP.

The term biosensor generally refers to a device that uses specific biochemical reactions mediated by isolated enzymes, immunosystems, tissues, organelles or whole cells to detect chemical compounds, usually by electrical, thermal or optical signals. As used herein a "biosensor" refers to a protein capable of binding to analyte (for example, glucose or galactose) which may be used to detect analyte or a change in analyte concentration by a detector means as herein described.

The term "binding proteins" refers to proteins which interact with specific analytes in a manner capable of providing or transducing a detectable and or reversible signal differentiable either from when analyte is not present, analyte is present in varying concentrations over time, or in a concentration-dependent manner, by means of the methods described. The detection of signal event includes continuous, programmed, and episodic means, including one-time or reusable applications. Reversible signal generation or detection may be instantaneous or may be time-dependent providing a correlation with the presence or concentration of analyte is established. Binding proteins mutated in such a manner to effect such signals are preferred.

The term "Galactose/Glucose Binding Protein" or "GGBP" as used herein refers to a type of protein naturally found in the periplasmic compartment of bacteria. These proteins are naturally involved in chemotaxis and transport of small molecules (e.g., sugars, amino acids, and small peptides) into the cytoplasm. GGBP is a single chain protein consisting of two globular/domains that are connected by three strands to form a hinge. The binding site is located in the cleft between the two domains. When glucose enters the binding site, GGBP undergoes a conformational change, centered at the hinge, which brings the two domains together and entraps glucose in the binding site. X-ray crystallographic structures have been determined for the closed form of GGBP from *E. coli* (N. K. Vyas, M. N. Vyas, F. A. Quiocho Science 1988, 242, 1290-1295) and *S. Typhimurium* (S. L. Mowbray, R. D. Smith, L. B. Cole Receptor 1990, 1, 41-54) and are available from the Protein Data Bank on the world wide web at www.rcsb.org/pdb/ as 2 GBP and 3 GBP, respectively. The wild type *E. coli* GGBP DNA and amino acid sequence can be found on the world wide web at www.ncbi.nlm.nih.gov/entrez/ accession number D90885 (genomic clone) and accession number 23052 (amino acid sequence). Preferred GGBP is from *E. coli*.

"Mutated Binding Protein" (for example "mutated GGBP") as used herein refers to binding proteins from bacteria containing an amino acid(s) which has been substituted for, deleted from, or added to the amino acid(s) present in naturally occurring protein. Exemplary mutations of binding proteins include the addition or substitution of cysteine groups, non-naturally occurring amino acids (Turcatti, et al. J. Bio. Chem. 1996 271, 33, 19991-19998) and replacement of substantially non-reactive amino acids with reactive amino acids to provide for covalent attachment to surfaces.

Exemplary mutations of the GGBP protein include a cysteine substituted for a lysine at position 11 (K11C), a cysteine substituted for aspartic acid at position 14 (D 14C), a cysteine substituted for valine at position 19 (VI 9C), a cysteine substituted for asparagine at position 43 (N43C), a cysteine substituted for a glycine at position 74 (G74C), a cysteine substituted for a tyrosine at position 107 (Y107C), a cysteine substituted for threonine at position 110 (T110C), a cysteine substituted for serine at position 112 (S112C), a double mutant including a cysteine substituted for a serine at position 112 and serine substituted for an leucine at position 238(S1 12C/L238S), a cysteine substituted for a lysine at position 113 (K113C), a cysteine substituted for a lysine at position 137 (K137C), a cysteine substituted for glutamic acid at position 149 (E149C), a double mutant including a cysteine substituted for an glutamic acid at position 149 and a serine substituted for leucine at position 238 (E149C/L238S), a double mutant comprising a cysteine substituted for histidine at position 152 and a cysteine substituted for methionine at position 182 (H152C/M182C), a double mutant including a serine substituted for an alanine at position 213 and a cysteine substituted for a histidine at position 152 (H152C/A213S), a cysteine substituted for an methionine at position 182 (M182C), a cysteine substituted for an alanine at position 213 (A213C), a double mutant including a cysteine substituted for an alanine at position 213 and a cysteine substituted for an leucine at position 238 (A213C/L238C), a cysteine substituted for an methionine at position 216 (M216C), a cysteine substituted for aspartic acid at position 236 (D236C), a cysteine substituted for an leucine at position 238 (L238C) a cysteine substituted for a aspartic acid at position 287 (D287C), a cysteine substituted for an arginine at position 292 (R292C), a cysteine substituted for a valine at position 296 (V296C), a triple mutant including a cysteine substituted for an glutamic acid at position 149 and a alanine substituted for a serine at position 213 and a serine substituted for leucine at position 238 (E149C/A213S/L238S), a triple mutant including a cysteine substituted for an glutamic acid at position 149 and a alanine substituted for an arginine at position 213 and a serine substituted for leucine at position 238 (E149C/A213R/L238S).

The mutated binding protein or GGBPs of the present invention may be used in an in vitro or in vivo analyte assay which, for example, is capable of following the kinetics of biological reactions involving an analyte or glucose, as well as in clinical assays and food or beverage industrial testing.

The mutation may serve one or more of several purposes. For example, a naturally occurring protein may be mutated in order to change the long-term stability of the protein; to conjugate, bind, couple, or otherwise associate the protein to a particular encapsulation matrix, polymer; or surface, or to adjust its binding constant with respect to a particular analyte, and combinations thereof.

In the instant invention, analyte and mutated protein act as binding partners. The term "associates" or "binds" as used herein refers to binding partners having a relative binding constant (Kd) sufficiently strong to allow detection of binding to the protein by a detection means. The Kd may be calculated as the concentration of free analyte at which half the protein is bound, or visa versa. When the analyte of interest is glucose, the Kd values for the binding partners are preferably between about 0.0001 mM to about 20 mM.

In the present invention, it has been shown that mutated GGBPs may be used to detect glucose binding by attaching the protein to a sensor surface through the thiol group which provides a detectable signal upon glucose binding. To "provide a detectable signal", as used herein refers to the ability to recognize a change in a property of a sensor surface/protein combination in a manner that enables the detection of ligand-protein binding. For example, in one embodiment, the mutated GGBPs are attached to a sensor surface whose detectable characteristics, for example, refractive index, alters upon a change in protein conformation which occurs on glucose binding.

Mutated GGBPs may be engineered to have a histidine tag on the proteins N-terminus, C-terminus, or both termini. Histidine fusion proteins are widely used in the molecular biology field to aid in the purification of proteins. Exemplary tagging systems produce proteins with a tag containing about six histidines and preferably such tagging does not compromise the binding activity of the mutated GGBP.

In one aspect of the present invention, the biosensor is used for analyte sensing in vivo. In this aspect, the biosensor is encapsulated into a matrix which may then be used as an implantable device. The "matrix" can be in any desirable form or shape including a disk, cylinder, patch, microsphere, porous polymer, open cell foam or the like, providing it permits permeability to analyte. The matrix additionally prevents leaching of the biosensor. The matrix permits light from optical sources or any other interrogating light to or from the protein to pass through the biosensor. When used in an in vivo application, the biosensor will be exposed to a substantially physiological range of analyte and determination or detection of a change in analyte concentration would be desired whereas the determination or detection includes continuous, programmed, and episodic detection means. Thus, the envisioned in vivo biosensor of the present invention comprises at least one mutated binding protein and at least one thiol group for attachment to a sensor surface in an analyte permeable entrapping or encapsulating matrix such that the mutated binding protein provides a detectable and reversible signal change when the mutated binding protein is exposed to varying analyte concentrations, and the detectable and reversible signal can be related to the concentration of the analyte.

The binding protein biosensors of this invention are capable of measuring or detecting micromolar ($10^{-6}$ molar) to molar analyte concentrations without reagent consumption. In some embodiments, their sensitivity to analyte may enable the biosensors to be used to measure the low analyte concentrations known to be present in low volume samples of interstitial or ocular fluid and perspiration. The implantable biosensors may, in some embodiments, be implanted into or below the skin of a mammal's epidermal-dermal junction to interact with the interstitial fluid, tissue, or other biological fluids. The binding protein biosensors of the present invention provide for the means to monitor analyte continuously, episodically, or "on-demand" as would be appropriate to the user or to the treatment of a condition.

In other embodiments, the biosensors sensitivity to analyte (for example glucose) is such that they may be used to test blood analyte levels.

In other embodiment, mutated protein may be used to detect analyte binding by measuring refractive index change. "Refractive index" is used in its common meaning, i.e., the ratio of the velocity of a specific radiation in a vacuum to the velocity in a given medium. The direction of a ray of light is changed i.e., refracted, upon passage from one medium to another of different density or when traversing a medium whose density is not uniform. Suitable detection or measuring devices for refractive indexes are reflectance spectrophotometers, and other refractive index-based detection means, for example, surface plasmon resonance and long period grating means.

In one aspect of the present invention, Surface Plasmon Resonance (SPR) is used to monitor such refraction. SPR may be used to determine the binding specificity between two molecules, assess how much of a given molecule is present and active, and quantitatively define both the kinetics and affinity of binding. SPR may be used to visualize the progress of biomolecular binding through time by defining the change in mass concentration that occurs on a sensor surface during the binding and dissociation process.

SPR is based upon the phenomenon of total internal reflection, wherein light traveling though a medium of higher refractive index e.g., glass, is totally internally reflected upon encountering a medium of lower refractive index e.g., solution, at a sufficiently oblique angle. In SPR detection, the intensity of the reflected light is dampened by the presence of a metal surface at the interface of the two media. The decrease in intensity occurs at a well-defined angle, which is dependent on the refractive indices of the two media, referred to as the "resonance angle". As proteins adsorb at the interface of the two media, the refractive index of the solution near the interface changes, shifting the angle at which the reflected light is dampened, i.e., shifting the resonance angle.

In one embodiment, the configuration used with SPR consists of a prism coated with a thin metal film. In one aspect of the present invention, GGBP or binding protein is immobilized onto this surface.

As used herein, "sensor surface" refers to the location upon which at least one binding partner is immobilized for the purpose of measuring the refractive index. The sensor surface comprises a substrate which may be comprised of glass or plastic, upon which is layered a suitable metal having conduction band electrons capable of resonating with light at a suitable wavelength. A variety of metallic elements satisfy this condition. They include, but are not limited to silver, gold, copper, cobalt, aluminum, and the like. In one embodiment the sensor surface is a removable microchip. This transducing element configuration may be for example, incorporated at the distal end of a fiber or other small minimally invasive probe to be inserted within the tissue of a patient to enable an episodic, continuous, or programmed reading, or combinations thereof to the patient.

In an exemplary case, the mutated GGBP(s), in one embodiment may be immobilized onto a sensor surface covered with a matrix of carboxymethylated dextran covalently attached to the sensor surface to form a flexible hydrogel of estimated thickness 100-200 nm or 200-400 nm. This dextran matrix can be derivatized to give a number of different functional groups and to allow for a variety of immobilization chemistries. In one embodiment, the procedure utilizes activation of the carboxy groups of the dextran gel with a mixture of N-hydroxysuccinimide and N-ethyl-N' (dimethylaminopropyl)carbodiimide to form NHS esters, which enables coupling to the amino groups on proteins.

In another embodiment the sensor surface composition is comprised of a carboxymethyl layer positioned on a chip.

Additional immobilization methods which may be used in the present invention include coupling by thiol/disulfide exchange, aldehyde coupling, hydrazide group coupling, sulfhydryl group coupling and chelate linkage of oligohistidine tags.

In a preferred embodiment, the immobilization of mutated binding protein is achieved by creating a thiol coupling/disulfide bond to any of the herein described cysteine residues of the mutated binding protein with the sensor surface or an adjacent layer thereon.

In one embodiment, after successful immobilization of the mutated GGBP on the sensor surface, a kinetic analysis may be conducted. Typically, several different concentrations of analyte are injected over the sensor surface in duplicate or triplicate. For example, glucose, at a constant concentration, is introduced into a buffer flow above the sensor surface and the progress of complex formation at the sensor surface is monitored. This procedure may be followed by a dissociation phase, in which the free glucose is absent from the buffer and the time-course of complex dissociation is recorded. Finally, the sensor surface may be regenerated (for example by a short exposure to a buffer at low pH) to remove the remaining complex. The cycle of association experiment, dissociation experiment, and regeneration may be repeated using different concentrations of glucose. Light is shone on the reverse side of the sensor surface, propagating an electron charge density wave phenomenon that arises at the surface of the metallic film. This takes the form of an evanescent wave that extends beyond the sensor surface and detects mass changes on the surface. A sequence of binding-progress curves may be obtained containing information on chemical rate constants and on the thermodynamic equilibrium constant of the interaction.

Binding-progress curves may also be referred to as sensorgrams in one embodiment where the BIACORE (Uppsala, Sweden) apparatus is used. In this embodiment, software is available with this system that may be used to fit the data to a range of binding models and the Kd may be calculated.

The time-dependent change of the refractive index in the vicinity of the surface upon binding is commonly measured in RU (resonance units), with 1 RU corresponding approximately to 1 pg protein/mm$^2$.

In another embodiment, the concentration of analyte in a biological solution or other solution may be determined using SPR. As used herein, a "biological solution" includes but is not limited to blood, perspiration, and or ocular or interstitial fluid including combinations thereof.

Commercial apparatuses using SPR to assess binding between partners are currently available (those made by Biacore, Uppsala, Sweden (BIACORE); and Intersens Instruments BV, Amersfoort, Netherlands (IBIS), Texas Instruments, and several laboratory-built SPR instruments. A recent review by Myszka et al. of such devices is found in J. Mol. Recognit. 2001 14: 261-268.

In an alternative embodiment, refractive index may be measured using optical fiber long period grating (LPG) to detect binding between analyte and the mutated GGBP of the present invention by applying affinity coatings containing the mutated proteins to a fiber containing sensor surface (for example, commercially available equipment from Luna Innovations, Inc., Blacksburg, Va. and see also M. E. Jones, et al. 2000, NSF Design and Manuf. Research Conf., Vancouver, Poster Number SBIR-510). The LPG scatters out light at a particular wavelength based on grating period, fiber refractive index and the refractive index of the surrounding medium. As affinity coating absorbs the target molecule the refractive index changes and causes a shift in the wavelength of scattered light seen by the LPG. Monitoring of the LPG fiber sensor may be accomplished through a Lunascan system (Luna Innovations, Inc.) consisting of a spectrometer, detector, controller, laptop computer with interface and switching mechanism for interrogation of multiple LPG sensors. Attachment or surface immobilization of one or more mutated binding proteins by the above-mentioned techniques to LPG fiber, either at the distal end or one or more positions along the fiber length is understood as yet another embodiment of the present invention.

In other embodiment the detection device may be a quartz crystal microbalance (QCM) containing a suitable layer thereon for thiol coupling of mutant protein. Suitable QCM devices are illustrative of those described by Guilbault in Biosensors & Bioelectronics 1999 14, 633-670.

EXAMPLES

The following examples illustrate certain preferred embodiments of the instant invention, but are not intended to be illustrative of all embodiments.

Example 1

This Example Describes the Method for the Expression and Purification of Mutant Proteins without Histidine Tags.

GGBP is coded by the Mg1B-1 gene in *E. coli*. This protein was altered by introducing the amino acid cysteine at various positions through site-directed mutagenesis of the a Mg1B-1 gene. These proteins were then expressed in *E. coli* and purified.

Cassette mutagenesis of Mg1B-1 was accomplished as follows. The wild-type Mg1B-1 gene was cloned into a pTZ 18R vector (Dr. Anthony Cass, Imperial College, London, England). Mutant plasmids were generated from this parent plasmid using cassette mutatgenesis producing randomized amino acid sequences, essentially as described by Kunkel (1991) and cloned in *E. coli* JM109 (Promega Life Science, Madison, Wis.). Mutant plasmids were identified by sequencing. The mutant protein was induced in JM109 and purified as described below. An *E. coli* JM109 colony containing the mutant plasmid was grown overnight at 37° C. with shaking (220 rpm) in LB broth containing 50 tg/mL ampicillin (LB/Amp). The overnight growth was diluted 1:100 in 1 L fresh LB/Amp and was incubated at 37° C. with shaking until the OD600 of the culture was 0.3-0.5. Expression of the mutant was induced by the addition of 1 mM IPTG (Life Technologies, Gaithersburg, Md.) final concentration with continued incubation and shaking at 37° C. for 4-6 hours. The cells were harvested by centrifugation (10,000×g, 10 min, 4° C.).

The mutant protein was harvested by osmotic shock and was purified by column chromatography. The cell pellet was resuspended in a sucrose buffer (30 mM Tris-HCL pH 8.0, 20% sucrose, 1 mM EDTA), incubated at room temperature for 10 min, and then centrifuged (4000×g, 15 min, 4° C.). The supernatant was poured off and kept on ice. The cell pellet was resuspended, and 10 mL ice cold, sterile deionized $H_2O$ was repeated, and the suspension was incubated on ice and centrifuged. The remaining supernatant was pooled with the other collected supernatants and was centrifuged once again (12,000×g, 10 min, 4° C.). The pooled shockate was filtered through a 0.8 μm and then a 0.45 cm filter. Streptomycin sulfate (Sigma Chemical Co., St. Louis, Mo.), 5% w/v, was added to the shockate and was stirred once for 30 min followed by centrifugation (12,000×g, 10 min, 4° C.). The shockate was then concentrated using the Amicon Centriprep 10 (10,000 MWCO) filters (Charlotte, N.C.) and dialyzed overnight against 5 mM Tris-HCl pH 8.0, 1 mM MgC12. The dialyzed shockate was centrifuged (12,000×g, 30 min, 4° C.). The resulting supernatant was added to a pre-equilibrated DEAE Fast Flow Sepharose column (Amersham Pharmacia Biotech, Piscataway, N.J.) at 0.5 mL/min. The column was washed with 5-10 column volumes. A linear gradient from 0-0.2 M NaCl was applied to the column and fractions were collected. The mutant protein containing fractions were identified by SDS-PAGE with Coomassie Brilliant Blue staining (mw. Approx. 32 kDa). The fractions were pooled and dialyzed overnight (4° C.) against phosphate buffered saline (PBS) or 10 mM ammonium bicarbonate (pH 7.4) and concentrated using Amicon Centriprep 10 filters, and stored at 4° C. or −20° C. with glycerol. The ammonium bicarbonate dialyzed protein was lyophilized.

Example 2

This Example Describes the Expression and Purification of Mutant GGBPs Containing Histidine Tags.

GGBP mutants were engineered by either site-directed mutagenesis or the cassette mutagenesis. Site-directed mutagenesis (QuikChange, Stratagene, La Jolla, Calif.) was performed to alter individual amino acids in the pQE70 vector by replacing one amino acid with another, specifically chosen amino acid. The cassette mutagenesis method (Kunkel) was performed to randomize amino acids in a specified region of the GGBP gene. The mutated cassettes were then subcloned into the pQE70 expression vector.

The pGGBP-His plasmid contained the GGBP gene cloned into the pQE70 expression vector (Qiagen, Valencia, Calif.). This construct places six histidine residues on the C-terminus of the GGBP gene. *E. coli* strain SG1 3009 was used to over express mutant GGBP-His following standard procedures (Qiagen). After over expression of a 250 mL culture, the cells were collected by centrifugation (6000 rpm) and resuspended in 25 mL bugbuster (Novagen, Madison, Wis.). Lysozyme (25 mg was added to the lysate and the mixture was gently mixed at room temperature (RT) for 30 min. Clear lysate was produced by centrifugation (6000 rpm) and to this, 0.5 ml imidizole (1 M) and 3 ml of Ni-NTA beads (Qiagen) was added. After 30 minutes of gently mixing at RT, the mixture was centrifuged (6000 rpm) and the lysate removed. The beads were washed with 25 ml of solution (1M NaCl, 10 mM tris, pH 8.0) and recentrifuged. The mutant GGBP-His was eluted from the beads by adding 5 mL solution (160 mM imidazole, 1 M NaCl, 10 mM Tris, pH 8.0) and mixing for 15 min. The protein solution was immediately filtered through a Centriplus YM-100 filter (Amicon, Charlotte, N.C.) and then concentrated to 1-3 mg/ml using a Centriplus YM-10 filter. The protein was dialyzed overnight against 2 L of storage solution (1 M NaCl, 10 mM Tris, 50 mM $NaPO_4$, pH 8.0).

Proteins were immobilized onto a carboxymethyldextran (CM5) sensor surface (BIACORE) by thiol coupling using standard thiol coupling chemistry with a flow rate of 5 μl/min in 10 mM HEPES pH 7.4, 150 mM NaCl, 0.05% BIACORE Surfactant P20 (BIAcore) (HBS-P) running buffer. The sensor surface was activated with a 2 minute pulse of ethanolamine (EDC/NHS) followed by a 4 min pulse of 80 mM 2-(2-pyridinyldithio) ethaneamine (PDEA), 0.1 M sodium borate pH 8.5, E149C GGBP (1.8 mg/ml) was injected at a 1:50 dilution in 10 mM sodium acetate pH 4.5 for various times. Carbonic anhydrase 11 (5 mg/ml) was injected at 1:10 dilution in 10 mM sodium acetate pH 4.5 for 20 minutes. G74C GGBP (2.6 mg/ml) was injected at 1:50 dilution in 10 mM sodium acetate pH 4.5 for 12 minutes. A213C GGBP (0.6 mg/ml) was injected at 1:20 dilution in 10 mM sodium acetate pH 4.5 for 2 4 minutes. A 4 minute pulse of 50 mM cysteine, 1 M NaCl, 0.1 M sodium formate pH 4.3 was used to quench the reaction and remove non-specifically bound protein from the surface. Following immobilization, the protocol DESORB (0.5% SDS, 50 mM glycine pH 9.5) was run to remove protein aggregates from the system. Surfaces of 3000 RU (E149C GGBP), 4500 RU (carbonic anydrase), 2000 RU (A213C GGBP), and 4000 RU (G74C GGBP) were used for experiments.

Proteins were immobilized onto a Carboxymethyldextran (CM5) sensor surface (BIAcore) by amine coupling using standard amine coupling chemistry with a flow rate of 5 μl/min in HBS-P running buffer. The surface was activated with a 7 minute pulse of EDC/NHS. Proteins (WT GGBP, 2 mg/ml; E149C GGBP, 1.8 mg/ml) were injected at a 1:50 dilution in 10 mM sodium acetate pH 4.5 for 20 minutes. A pulse of 1 M ethanolamine pH 8.0 was injected to quench the reaction and remove nonspecifically bound protein. Surfaces of 4800 RU for E149C and 2400 RU for wild type GGBP were used for experiments.

Thiol coupling of E149C GGBP on C1 surfaces was carried out as follows. E149C GGBP was immobilized on a carboxymethyl (C1) chip using standard thiol coupling chemistry with a flow rate of 5 μl/min in HBS-P running buffer. The C1 surface was activated with a 4 min pulse of EDC/NHS followed by a 4 min pulse of 80 mM PDEA of 0.1 M sodium borate pH 8.5. E149C GGBP (1.8 mg/ml) was injected at a 1:2 dilution in 10 mM sodium acetate pH 4.5 for 50 minutes at a flow rate of 1 μl/min. A 7 minute pulse of 50 mM cysteine, 1M NaCl, 0.1 M sodium formate pH 4.3 was used to quench the reaction and remove non-specifically bound protein from the surface. A surface of 9000 RU was used for experiments.

Amine coupling of E149C GGBP on C1 surfaces. E149C GGBP was immobilized on a C1 chip using standard amine coupling chemistry with a flow rate of 5 μl/min in HBS-P running buffer. The surface was activated with a 7 minute pulse of EDC/NHS. E149C GGBP (1.8 mg/ml) was injected at a 1:2 dilution in 1 0 MM sodium acetate pH 4.5 for 50 minutes at a flow rate of 1 μl/min. A pulse of 1 M ethanolamine pH 8.0 was injected to quench the reaction and remove nonspecifically bound protein.

All glucose injections were performed at 25° C. in the appropriate running buffer for the specific experiment. Glucose injections were 10 μl at a flow rate of 10 μl/min (1 minute contact time). Injections of different glucose concentrations were repeated three times and alternated between the protein and blank surfaces. The protein surface was regenerated by washing of the flow channel with running buffer followed by a running buffer injection. Sensorgrams were either blank surface subtracted or were double referenced by first subtracting the glucose injection over a blank surface from the corresponding glucose injection on the protein surface. A buffer injection over the blank surface was then subtracted from a buffer injection over the protein surface. The final sensorgram was obtained by subtracting the normalized buffer injection from the normalized glucose injection.

An active E149C GGBP surface (3000 RU) was denatured by continuous flow overnight with 1 M guanidine HCl, 10 mM HEPES pH 7.5, 0.5 mM EDTA. After unfolding of the protein, glucose injections were performed in HBS-EP. The glucose signal was restored by changing the running buffer to HBS-P, 1.5 mM $CaCl_2$ and running continuous flow overnight.

FIG. 1 depicts the effect of coupling strategies on glucose detection. In FIG. 1, immobilized proteins are shown with the coupling method in parentheses. Running buffer and 100 gM glucose were injected over the indicated surfaces during a one minute interval. Double referenced sensorgrams were averaged during the time frame corresponding between 10 and 50 seconds during the injection. Each injection was done in triplicate. As is evident from the figure, thiol-coupling for the mutated GGBP E149C results in significantly enhanced signal upon glucose binding in comparison to amino coupling or buffer only.

Figure 2:
FIG. 2 illustrates the SPR response of the thiol coupled E149C GGBP mutant protein upon binding a panel of sugars.

FIG. 2 depicts the specificity of E149C mutated GGBP to bind glucose preferentially. The indicated sugars were injected at a concentration of 100 μM on a 3000 RU thiol-coupled E149C surface. Double referenced sensorgrams were averaged during the time frame corresponding between 10 and 50 seconds during the injection. Each injection was done in triplicate. As is evident from the figure, glucose binds more readily to the thiol-coupled mutant than do the other sugars, indicating the selectivity of the mutant has been maintained.

Figure 3:
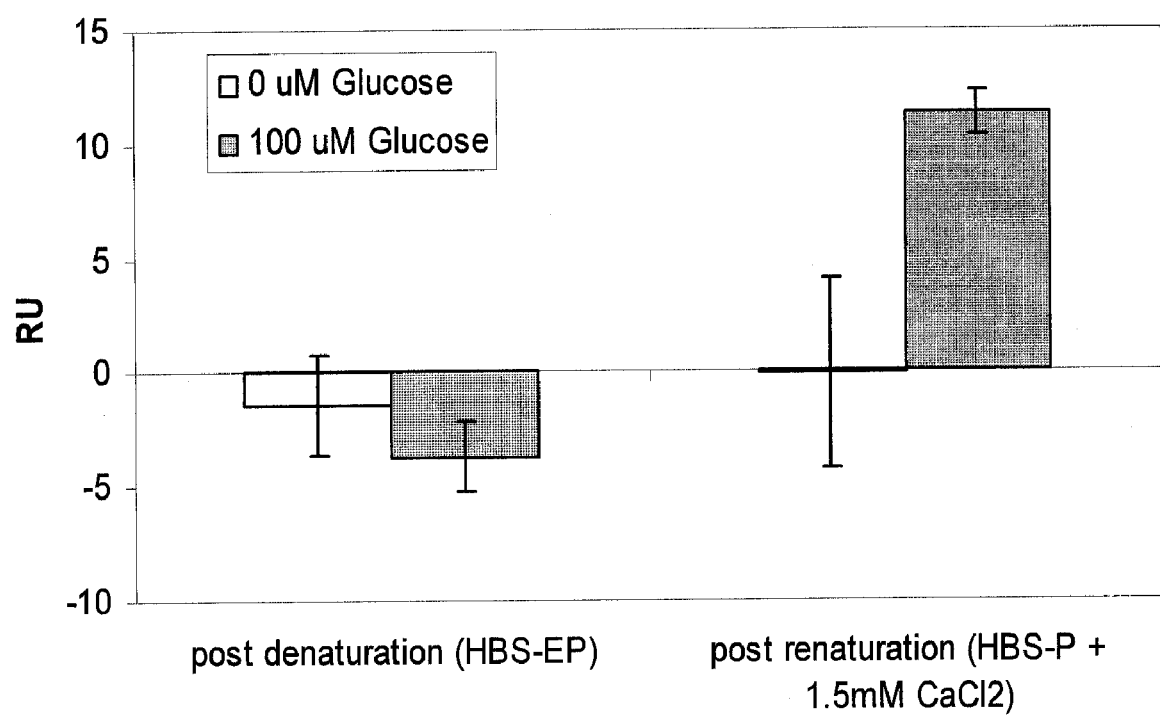
FIG. 3 illustrates the SPR response of the thiol coupled E149C GGBP mutant protein to glucose following denaturation and following renaturation with buffer in the presence of calcium chloride.

FIG. 3 depicts the results of glucose detection of the mutated GGBP, E149C mutant after denaturation and after renaturation. An active thiol-coupled E149 C GGBP surface was denatured according to the protocol outlined above. HBS-EP injections were performed following denaturation with 1 M guanidine HCL overnight. This method did not result in glucose signals. Glucose signals were restored following HBS-P and 1.5 mM $CaCl_2$ injections following continuous flow in running buffer overnight. Double referenced sensorgrams were averaged during the time frame corresponding between 10 and 50 seconds during the injection. Each injection was done in triplicate.

Figure 4:
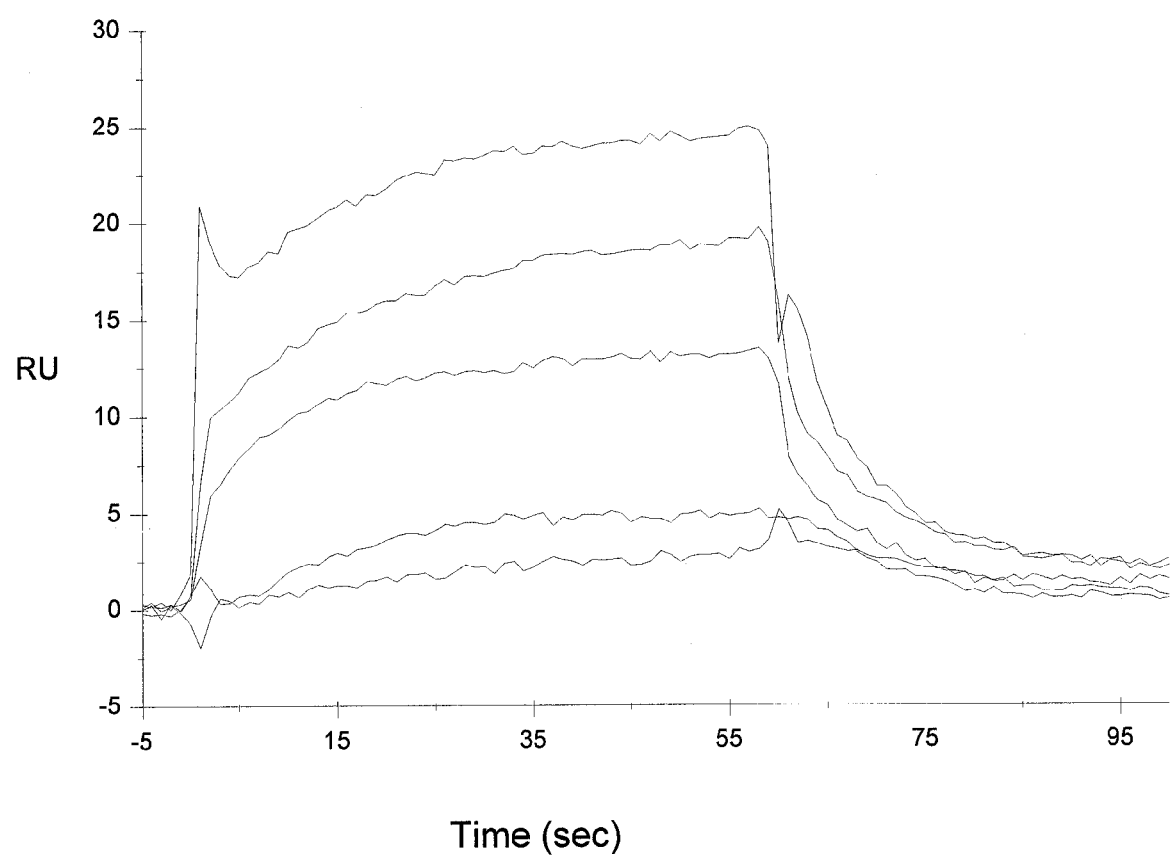
FIG. 4 illustrates the SPR response over time for injections of a range of glucose concentrations on the thiol coupled E149C GGBP surface.
Figure 5:
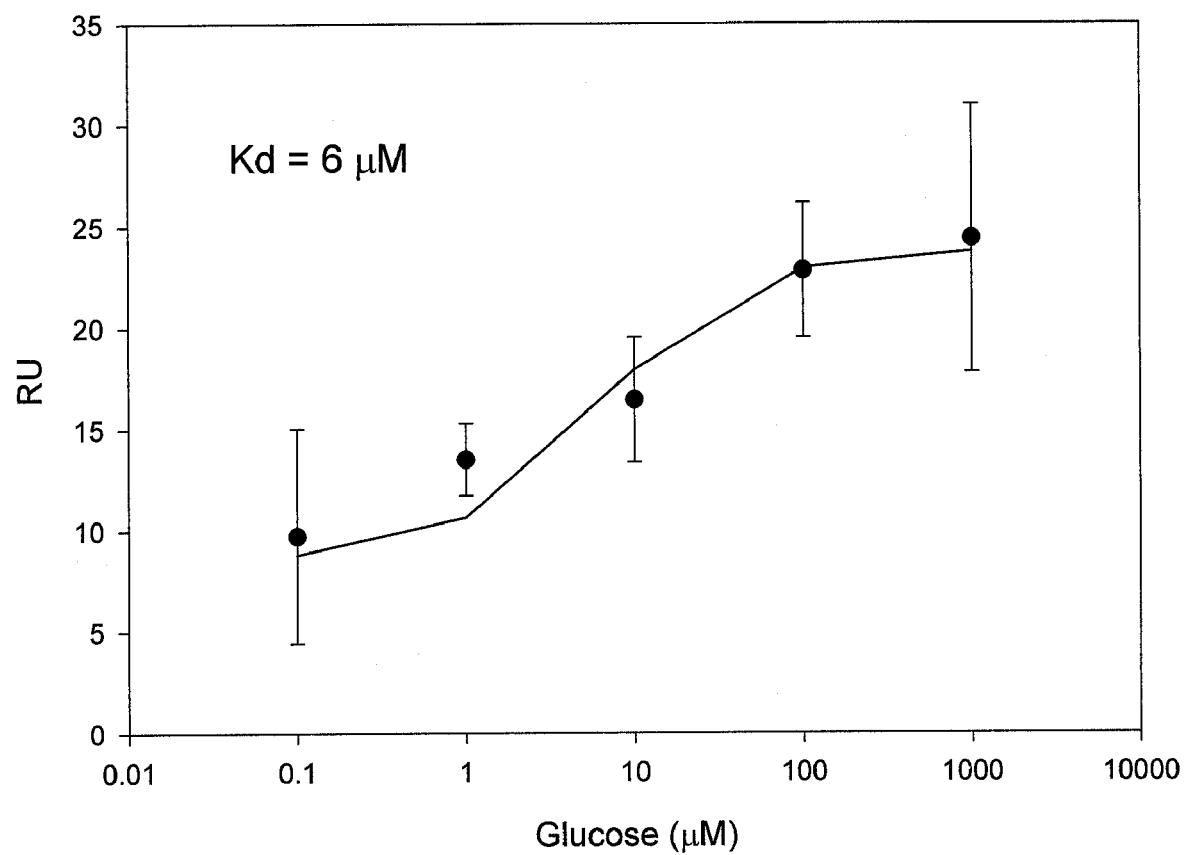
FIG. 5 illustrates a titration curve for the range of glucose concentrations in the data set illustrated in FIG. 4.

FIGS. 4 and 5 depict glucose titration on a thiol-coupled E149C GGBP surface. FIG. 4 shows a sensogram resulting from glucose injections at concentrations of 0, 0.1 μM, 1.0 μM, 10 μM and 1000 μM. Sensorgrams were normalized by subtracting the corresponding blank surface injection from the protein surface injection. FIG. 5 depicts a plot of glucose concentration versus response (RU). Blank subtracted sensorgrams were averaged during the time frame corresponding to between 10 and 50 seconds during the injection. Each injection was performed in triplicate.

Figure 6:
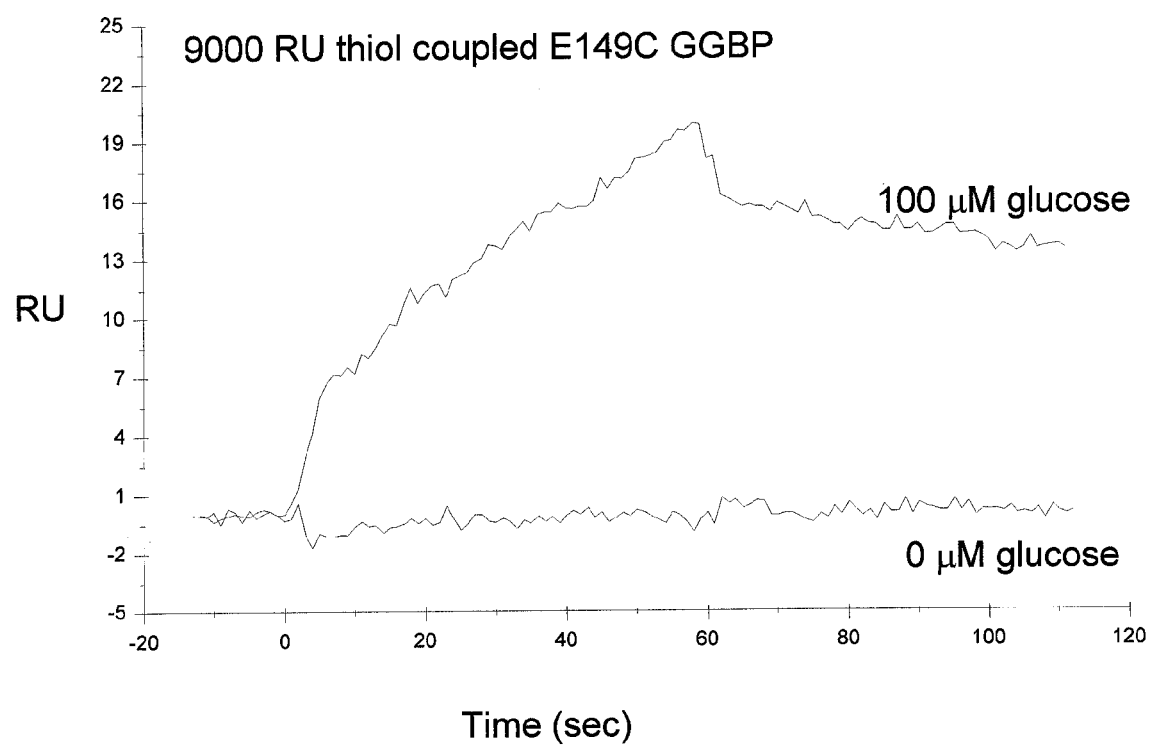
FIG. 6 illustrates the SPR response of a thiol coupled E149C GGBP mutant protein to glucose on a carboxymethyl surface (C1 chip).
Figure 7:
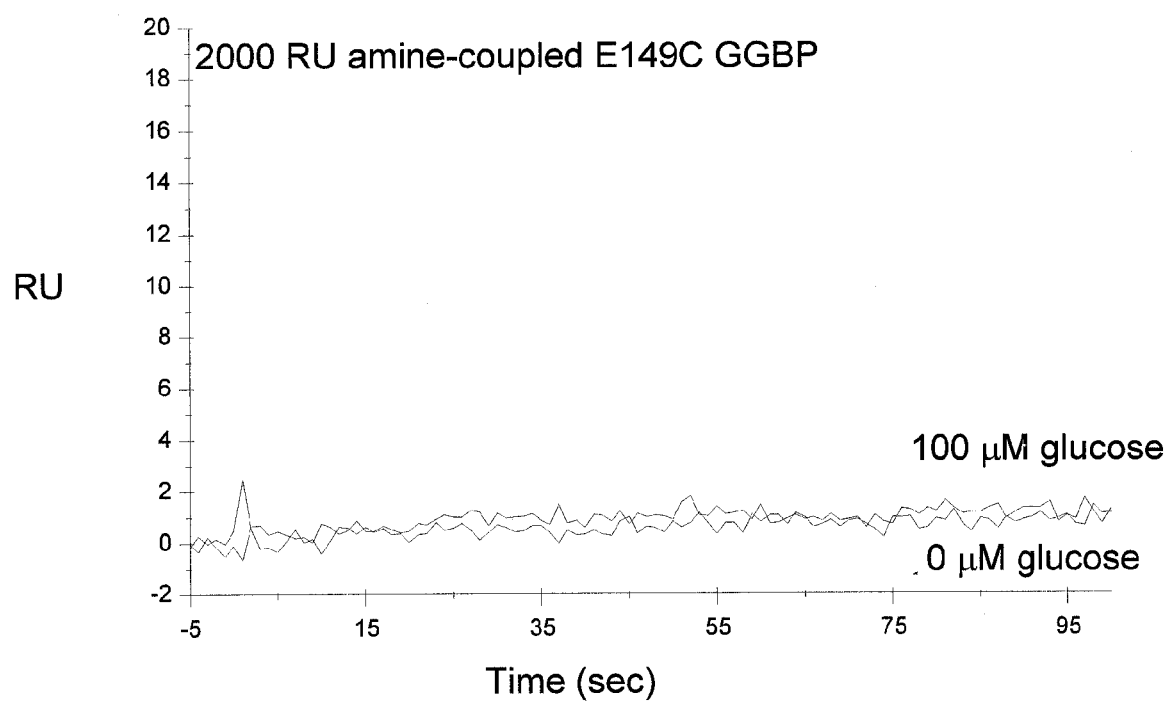
FIG. 7 illustrates the SPR response of an amine coupled E149C GGBP mutant protein to glucose on a carboxymethyl surface (C1 chip).

FIGS. 6 and 7 depict glucose detection on immobilized E149 C GGBP C1 surfaces. The sensorgram in FIG. 6 results from running buffer and 100 μM glucose injections over a 9000 RU thiol-coupled protein surface. Glucose detection is evident with this thiol-coupled surface; the sensorgram in FIG. 7, which shows the results from injection of running buffer and 100 μM glucose injected over a 2000 RU amine-coupled surface, does not result in glucose binding. Sensorgrams were double referenced.

Figure 8:
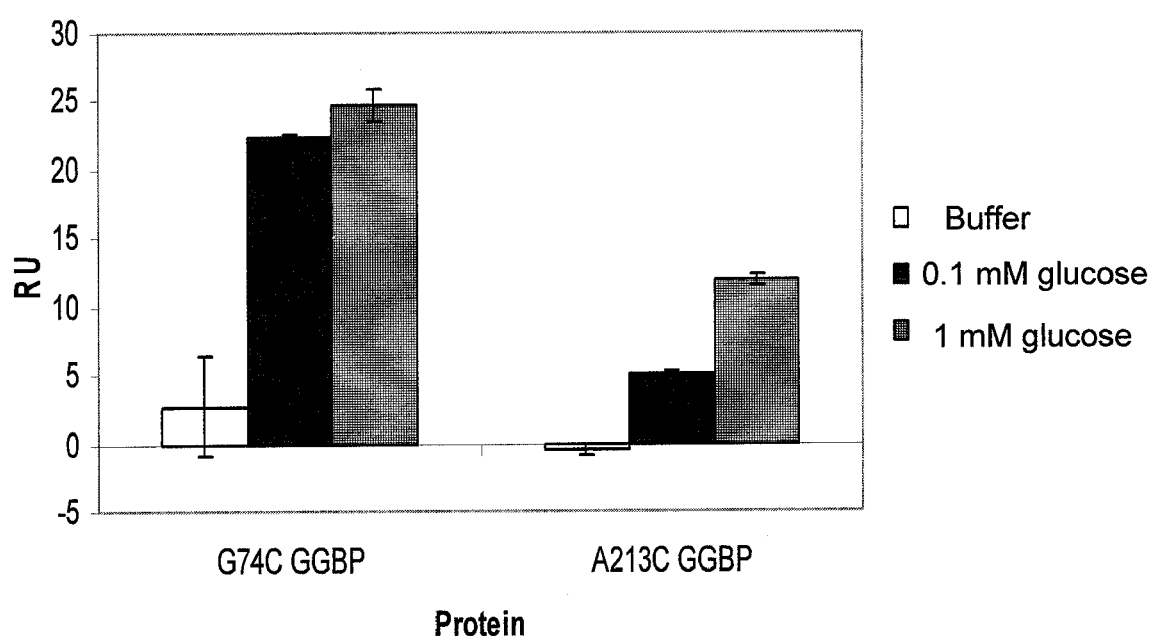
FIG. 8 illustrates glucose detection using SPR of thiol coupled G74C GGBP and thiol coupled A213C GGBP mutant proteins.

FIG. 8 depicts glucose detection by SPR using thiol-coupled mutants other than E149C. Both G74C and A213C mutants also resulted in signal-enhanced glucose detection. Running buffer with 0.1 mM and 1 mM glucose were injected over the indicated thiol-coupled surfaces during a one minute interval. Double referenced sensorgrams were averaged during the time frame corresponding between 10 and 50 seconds during the injection. Each injection was done in triplicate. A summary of the thiol mutants and their performance is given in Table 1. Non-thiol containing WT GGBP and denatured E149C GGBP proteins are representative negative controls (entries 3 and 7 respectively). As is shown in the table, in comparison to wild type and amine-coupled samples, the thiol-coupled mutated proteins of the instant invention show improvement in signal over background. In addition, the data indicated broad applicability to various sensor surfaces (see entries 1 and 9 of thiol coupled protein to CM5 and C1 surface).

TABLE 1

| Entry # | Surface | Attachment chemistry | Chip | RU immobilized | SPR Signal at Saturating Amounts of Glucose | |
|---|---|---|---|---|---|---|
| | | | | | Buffer | RU/glucose |
| 1 | E149C GGBP $H_6$ | Thiol | CM5 | 3000 | −0.5 ± 4.3 | 17.7 ± 0.5/ 100 μM |
| 2 | E149C GGBP $H_6$ | Amine | CM5 | 4800 | 1.4 ± 3.1 | 2.1 ± 5.5/ 100 μM |
| 3 | WT GGBP $H_6$ | Amine | CM5 | 2400 | 2.9 ± 1.5 | 5.9 ± 2.3/ 100 μM |
| 4 | G74C GGBP $H_6$ | Thiol | CM5 | 4000 | 2.7 ± 3.6 | 22.3 ± 0.2/ 100 μM |
| 5 | K137C GGBP $H_6$ | Thiol | CM5 | 4000 | 4.8 ± 3.2 | 9.5 ± 4.2/ 100 μM |
| 6 | A213C GGBP $H_6$ | Thiol | CM5 | 3000 | −0.5 ± 0.4 | 119 ± 0.4/ 1 mM |
| 7 | E149C GGBP $H_6$ denatured surface (neg control) | Thiol | CM5 | 3000 | −1.4 ± 2.2 | 0 ± 4.1/ 100 μM |
| 8 | E149C GGBP $H_6$ refolded protein surface | Thiol | CM5 | 3000 | −3.7 ± 1.5 | 11.4 ± 1.0/ 100 μM |
| 9 | E149C GGBP $H_6$ | Thiol | C1 | 9000 | 0.8 ± 1.5 | 10.2 ± 2.8/ 100 μM |
| 10 | E149C GGBP $H_6$ | Amine | C1 | 2000 | 0.4 ± 3.1 | −4.9 ± 5.3/ 1 mM |

SPR signal has been blank subtracted or double referenced.

What is claimed is:

1. A biosensor comprising:
   a. at least one mutated glucose/galactose binding protein having at least one substituted or added cysteine group; and
   b. at least one sensor surface wherein said mutated binding protein is coupled through said cysteine group to said at least one surface;
   wherein said at least one sensor surface comprises a metal layer having conduction band electrons capable of resonating with light, thereby providing a detectable signal.

2. The biosensor of claim 1 wherein said metal layer comprises silver or gold.

3. The biosensor of claim 1 wherein said analyte is glucose or galactose.

4. The biosensor of claim 1 wherein said mutated glucose/galactose binding protein has one amino acid substitution.

5. The biosensor of claim 1 wherein said mutated glucose/galactose binding protein has at least two amino acid substitutions.

6. The biosensor of claim 1 wherein said mutated glucose binding protein includes one amino acid substitution selected from the group consisting of a cysteine at position 11, a cysteine at position 14, a cysteine at position 19, a cysteine at position 43, a cysteine at position 74, a cysteine at position 107, a cysteine at position 110, a cysteine at position 112, a cysteine at position 113, a cysteine at position 149, a cysteine at position 213, a cysteine at position 216, a cysteine at position 238, a cysteine at position 287, and a cysteine at position 292.

7. The biosensor of claim 4 wherein said mutated binding protein has at least one histidine tag.

8. The biosensor of claim 1 wherein said mutated glucose/galactose binding protein includes a cysteine present at position 213.

9. The biosensor of 8 wherein said mutated glucose/galactose binding protein further includes a histidine tag.

10. The biosensor of claim 1 wherein said mutated glucose/galactose binding protein includes a cysteine present at position 149 coupled to said sensor surface.

11. The biosensor of claim 10 wherein said mutated glucose/galactose binding protein further includes a histidine tag.

12. The biosensor of claim 5 wherein said mutated glucose/galactose binding protein includes at least two amino acid substitutions selected from the group consisting of: a cysteine at position 112 and a serine at position 238, a cysteine at position 149 and a serine at position 238, a cysteine at position 152 and a cysteine at position 182, a cysteine at position 152 and a serine at position 213, a cysteine at position 213 and a cysteine at position 238, a cysteine at position 149 and an arginine at position 213, a cysteine at position 149 and a serine at position 213 and a serine at position 238, and a cysteine at position 149 and an arginine at position 213 and a serine at position 238 coupled to said sensor surface.

13. The biosensor of claim 12 wherein said mutated glucose/galactose binding protein further includes a histidine tag.

* * * * *